United States Patent [19]
Eibl et al.

[11] Patent Number: 5,895,653
[45] Date of Patent: Apr. 20, 1999

[54] ADJUVANT BASED ON COLLOIDAL IRON COMPOUNDS

[75] Inventors: Johann Eibl; Heinz Leibl; Josef Mannhalter, all of Vienna, Austria

[73] Assignee: Tempo G, Los Angeles, Calif.

[21] Appl. No.: 08/622,013

[22] Filed: Mar. 26, 1996

[30] Foreign Application Priority Data

Mar. 27, 1995 [DE] Germany .................. 195 11 276

[51] Int. Cl.⁶ .................. A61K 39/12; A61K 33/26
[52] U.S. Cl. .................. 424/204.1; 424/234.1; 424/278.1; 424/282.1; 424/283.1
[58] Field of Search .................. 424/204.1, 234.1, 424/278.1, 281.1, 282.1, 283.1

[56] References Cited

U.S. PATENT DOCUMENTS

| | | | |
|---|---|---|---|
| Re. 35,338 | 9/1996 | Haynes | 424/450 |
| 4,313,734 | 2/1982 | Leuvering . | |
| 4,452,773 | 6/1984 | Molday | 424/1.37 |
| 4,951,675 | 8/1990 | Groman et al. | 424/9.52 |
| 5,178,882 | 1/1993 | Kossovsky et al. | 424/494 |

FOREIGN PATENT DOCUMENTS

| | | |
|---|---|---|
| 0363835B1 | 4/1990 | European Pat. Off. . |
| 1041647 | 12/1965 | Germany . |
| 1 249 558 | 10/1971 | United Kingdom . |
| WO 94/15635 | 7/1994 | WIPO . |

OTHER PUBLICATIONS

Mancini Et Al., Immunochemistry, vol. 2, pp. 235–254 (1965).

Nakamura Et Al., Nature, vol. 307, pp. 381–382 (Jan. 26, 1984).

Good Et Al., J. of Immunology, vol. 141(3):972–977 (Aug. 1, 1988).

Gemant, A., Iron hydroxide: Model for enzymes that oxidize proteins. Molec. Biol. Rep. 4(2):121–125, 1978.

*Primary Examiner*—Donna C. Wortman
*Attorney, Agent, or Firm*—Thomas I. Rozsa; Tony D. Chen; Jerry Fong

[57] ABSTRACT

An adjuvant is described which comprises an iron compound in colloidal form as well as a pharmaceutical composition which comprises this adjuvant together with at least a protein and/or peptide and/or polysaccharide and/or a nucleic acid derived from a virus, bacterium and/or a parasite.

The adjuvant according to the invention and the pharmaceutical composition comprising this adjuvant are suitable for prophylactic or therapeutic treatment of illnesses caused by various pathogens.

15 Claims, No Drawings

ADJUVANT BASED ON COLLOIDAL IRON COMPOUNDS

DESCRIPTION

The present invention relates to colloidal iron compounds as adjuvants, a method for their production as well as pharmaceutical compositions comprising these.

BACKGROUND OF THE INVENTION

The term adjuvant is used to designate an auxiliary agent which when administered jointly with an antigen increases the immunogenicity of the antigen or influences the quality of the immune response. Adjuvants are administered with the intention of improving the immunogenicity of an antigen, i.e. to increase antibody formation and/or to induce a stronger cell mediated immune response to the antigen.

Customary adjuvants are aluminum compounds, lipid-containing compounds as well as inactivated Mycobacteria. Freund's adjuvant, a water-in-oil emulsion, is one of the most efficient adjuvants. This adjuvant is especially effective when Mycobacteria are suspended together with the antigen in the emulsion (Freund's complete adjuvant). However, a disadvantage of this adjuvant with use in humans is the possible appearance of chronic inflammation. On the other hand, emulsions without Mycobacteria (Freund's incomplete adjuvant) lead to lesser side-effects and are therefore already applied in humans.

A further group of adjuvants constitute suspensions of mineral salts to which the corresponding antigen is adsorbed. The customary adjuvants of this type are compounds of aluminum such as aluminum hydroxide, aluminum phosphate or aluminum sulfate.

Certain lymphokines also show adjuvant activity. For example, an increase in the immune response against malaria antigen by recombinant human interleukin-2 adsorbed to aluminum was reported by Good et al., J. Immunol. 141, 972–977, 1988. Nakamura et al., Nature 307, 381–382, 1984, demonstrated a 2- to 5-fold increase in antibody production against different antigens by gamma-interferon.

Aside from the immunological mode of action, the pharmacokinetics and/or biodegradability of the respective material are a further criteria for its suitability as an adjuvant. In general, materials which are subjected to metabolism in the organism are generally less toxic and tolerated very well locally. This is especially true for iron, which has been found to be the most important trace element in human and animal organisms. This iron commonly exists in the form of iron salts which are present in ionic form after intake into the body and can be reabsorbed very well.

Aside from the above mentioned adjuvants, further materials with adjuvant properties are also known. In EP-B-0363 835, a zinc hydroxide gel or iron hydroxide gel is described for adjuving an antigen solution. The adjuvant solution contains, for example, 1–45% (v/v) iron hydroxide gel and optionally lecithin. Starting from an $FeCl_3$ solution after sterile filtration, the adjuvant is obtained as a precipitate by adding NaOH or KOH up to a pH value of 6.0 to 7.8. The precipitated iron hydroxide gel is optionally homogenized by Ultra-Turrax®R treatment. However, a colloidal iron III hydroxide does not result from this treatment; instead, the substance is still present as a gel, as shown in comparative experiment 1. The iron hydroxide gel produced in this manner predominantly induces a humoral immune response. In addition, it is shown in comparative experiment 2 that the gel obtained according to EP-363 835 behaves differently in its protein adsorption than the colloidal solution according to the invention which is capable of binding a distinctly larger amount of protein.

U.S. Pat No. 4,452,773 describes ferromagnetic particles of $Fe_3O_4$ which are coated with water soluble polysaccharides and are of colloidal size. The particles have a diameter between 100 and 700 Å, possess a magnetic moment, are mono-dispersable and are stable against aggregation and degradation under physiological conditions. Based on their ferromagnetic properties, they are suitable for the labeling of cells or other biological materials. As a result of their different design and different properties these particles serve a completely different purpose and are especially used for labeling of biomolecules.

In WO-A-94 15 635, a pharmaceutical composition is described which comprises a particulate protein complex of a particulate component bound to a non-replicating protein antigen. The particulate component can, among other things, be a metal, preferably a metal from the transition elements scandium to copper or a corresponding metal oxide, especially iron oxide. The iron (III) oxide is present as a magnetic γ-oxide.

The adjuvants based on iron described in the prior art have the disadvantage that, on the one hand, the surfaces of the iron compounds are as a whole relatively small, which implies less adsorption of the antigen and, on the other hand, these compounds are poorly or less rapidly adsorbed by the organism.

SUMMARY OF THE INVENTION

An object of the present invention is to make available an adjuvant which is well tolerated and with which the immune response can be potentiated.

This object is achieved according to the invention with an iron compound in colloidal form.

Surprisingly, it was found that iron compounds in colloidal form are especially suitable for use in adjuvanting an antigen solution; the adjuvants obtained according to the invention are exceedingly stable, have good adsorbing and protein stabilizing properties, and potentiate the immune response, whereby protection against infections is ensured.

In accomplishing these and other objects, there is provided, in accordance with one aspect of the present invention, an adjuvant comprising an iron compound in a colloidal form. The iron in the iron compound can be in a trivalent form, and can be in the form of an iron hydroxide. The colloidal solution can be aqueous, or can be in a water-in-oil emulsion. Preferably, the particle size is 1 nm to 500 nm, more preferably 100 nm to 500 nm, and most preferably 200 nm.

In accordance with another aspect of the present invention, the adjuvant is suitable for parenteral administration. Additionally, the adjuvant can be suitable for mucosal administration, including oral administration.

In accordance with still another aspect of the present invention, the adjuvant is combined with at least an interleukin, an interferon, a cytokine, or any mixture thereof. Preferably, the interleukin, interferon and/or cytokine is adsorbed to the colloid.

The adjuvant according to the invention comprises iron compounds in colloidal form. The iron is preferably present in the iron compounds in trivalent form, is more preferably an inorganic iron compound and is most preferably essentially iron hydroxide. The iron compound according to the invention can also constitute a mixture of iron hydroxides and iron oxides which can be present in various hydration levels and modifications. Suitable anions of the iron compounds originally used, for example citrate ions, can also be contained in the colloid.

Materials in a state of dispersion in which the presence of dispersed particles is not macroscopically recognizable are understood as a colloidal form. A colloidal solution, also referred to as a sol, can pass through normal filters and also sterile filters, whereas they are held back by ultrafilters. According to the mode of particle mobility and interaction, the colloidal solutions according to the invention belong to the incoherent systems; in such systems, the majority of the particles are freely movable as a "kinetic unit" and not linked with any other particle.

Magnetic properties of the iron compound according to the invention are not necessary because the compound is not used as a label for a biomolecule but is surprisingly useful as an adjuvant.

Contrary to a labeling compound, the iron compound according to the present invention is not necessarily bound to the immunizing agent and can even be separately, e.g. simultaneously or successively, administered.

In a preferred embodiment the adjuvant according to the present invention does not possess magnetic, e.g. ferromagnetic properties or does possess the properties to a lower extent, respectively.

The solution according to the invention is preferably stored at 4° C. and stable. A solution whose particles do not sediment after several hours or days of standing is understood to be a stable colloidal solution.

Colloidal solutions are further characterized by the size of the particles, which is approximately between 1 nm and 500 nm. The particle size of the solution according to the invention is preferably between 100 nm and 500 nm, most preferably about 200 nm. The determination of particle size of the colloidal solution can be performed according to current methods, for example according to the principle of dynamic light scattering.

The adjuvant according to the invention is comprised of colloidal particles of defined composition which possess particularly good adsorbing properties and/or high binding capacity for antigens, for example proteins. As a result of the large total surface area of the adjuvant according to the invention, more protein can be adsorbed with a smaller amount of iron compound than is normally the case with customary carrier systems. Thereby, possible side-effects are also reduced.

The viscosity of the colloidal solution according to the invention is comparable with that of a protein solution and/or a 10–20% glycerin solution and is approximately 1 to 5 cP.

The adjuvant according to the invention is preferably present as an aqueous colloidal solution or also as a water-in-oil emulsion. The colloidal solution preferably has a pH value between 4.0 to 11.0, preferably 6.8 to 9.0, more preferably 7.0 to 8.5, most preferably 8.0. The choice of pH may be dependent on the protein or antigen used.

The water-in-oil emulsion is comprised for example of an iron compound in colloidal form, Freund's incomplete adjuvant and water. The ratio of aqueous colloidal to oil is for example 1:1, but all other mixture ratios are possible.

The adjuvant according to the invention or a pharmaceutical composition containing this is preferably present in a form suitable for parenteral administration. The parenteral administration can be performed for example in an intramuscular, subcutaneous, intradermal or intraperitoneal manner. The adjuvant is also suitable for the stimulation of mucosal immunity as it is induced by mucosal, for example oral, intranasal, intravaginal or intrarectal administration. The adjuvant can be used directly for these purposes, without further pretreatment, but also enclosed in capsules or liposomes. The adjuvant according to the invention and/or the finished pharmaceutical composition can also be made non-perishable by lyophilization. After reconstitution of the lyophilisate, a solution with the properties according to the invention is obtained.

The adjuvant according to the invention can additionally comprise at least one interleukin, interferon or other cytokine, for example interleukin-2, 4, 5, 7, 12 or interferon-γ. Mixtures thereof are also possible. The suitable cytokine and/or cytokine mixture is preferably adsorbed to the adjuvant. Adjuvant and cytokine are bound by covalent or non-covalent association.

Another aspect of the present invention includes a method for increasing the immunogenicity of an antigen, comprising the step of administering to a subject an antigen and an adjuvant solution containing a least one iron compound in colloidal form. The adjuvant should be administered to the subject at a time and dose sufficient to stimulate/potentiate the immune response to the antigen. The adjuvant can be administered along with the antigen.

Preferably, the iron in the iron compound is in a trivalent form, and can be a form of iron hydroxide. The adjuvant solution can be aqueous or be a water-in-oil emulsion. Preferably, the colloidal iron compound has a particle size ranging from 1 nm to 500 nm, more preferably has a particle size ranging from 100 nm to 500 nm, and still more preferably has a particle size of about 200 nm.

Another aspect of the present invention includes a method for producing an iron-containing adjuvant comprising the steps of altering the pH of a solution comprising an iron salt to obtain an iron colloid. The iron salt-containing solution can be aqueous, organic or a mixture of both. Preferably, the iron salt is a salt of a weak acid, such as iron citrate. Preferably, the pH of the solution is adjusted to 4.0 to 11.0, preferably 6.8 to 9.0, more preferably 7.0 to 8.5, and still more preferably to about 8.0. The choice of pH may be influenced by the protein or antigen to be employed. Preferably, the adjuvant produced according to the present method is subjected to sterile filtration or lyophilization.

The adjuvant according to the invention is obtainable by transforming a solution of an iron salt in a solvent into an iron compound in colloidal form by adjustment to a suitable pH value. As an iron salt, a salt of a weak acid is preferably used, especially iron citrate.

The solvent is preferably water or a mixture of water and an organic solvent preferably miscible with water such as, for example, ethanol or glycerol.

An acid which is incompletely dissociated in solution is understood to be a weak acid. The corresponding $pK_a$ value is larger than 2.0 and preferably lies between 20.0 and 2.0. Suitable salts are for example pyruvates, acetates or tartrates and especially citrates.

The adjuvant can be obtained by adjustment to a suitable pH value, whereby the pH value preferably lies between 7.0 and 9.0, and especially at about 8.0. The adjustment of the pH value can occur with suitable alkaline solutions, for example with NaOH, KOH, ammonia or bicarbonate.

An adjuvant according to the invention in the form of an oil-in-water emulsion can be produced by known methods by emulsifying an aqueous colloidal solution of the iron compound according to the invention with a suitable oil component, for example the oil component of Freund's adjuvant or with Freund's adjuvant.

For the production of an adjuvant according to the invention which additionally comprises at least an interleukin, interferon and/or other cytokine, the adjuvant as described above can be mixed, preferably as an aqueous colloidal solution, with a protein solution, preferably an aqueous protein solution.

The adjuvant according to the invention is preferably sterile filtered and/or lyophilized.

Subject matter of the invention is also a pharmaceutical composition which is characterized in that it comprises at least one protein and/or peptide and/or polysaccharide and/ or nucleic acid derived from a virus, bacterium and/or parasite and an adjuvant according to the invention optionally together with a suitable pharmaceutical carrier and/or diluent.

The virus is preferably selected from the group consisting of retroviruses, hepatitis viruses, flaviviruses, herpes viruses, influenza viruses, poxviruses, morbilliviruses, enteroviruses (polio virus) or paramyxoviruses. The virus is preferably present as a whole virus, virus-like particle or virus cleavage product. Virus-like particles are distinguished from a whole virus by the absence of genetic information, i.e. they contain no DNA. The virus-like particle can consist of proteins of the outer and, if present, inner virus coat as well as further viral proteins.

Virus cleavage products can be proteins or derivatives thereof, polysaccharides, peptides or nucleic acids derived from a virus and be from a native virus or be produced by means of recombinant techniques. The whole virus is preferably inactivated, attenuated or is a recombinant virus. The inactivation can be performed according to common methods, for example by chemical treatment.

The attenuation can be done for example by point mutation, site specific mutagenesis or deletion. According to common methods, the viruses or the virus cleavage products can also be produced recombinantly. As vectors for this, viruses such as, but not limited to, vaccinia viruses or adenoviruses, plasmids, cosmids or phages are used; the vehicle is equipped with suitable promoters, markers, etc.

The bacterium is preferably selected from the group consisting of E. coli, Bordetella, Borrelia, Pseudomonas, Haemophilus, Mycobacterium, Streptococci, Salmonella, Helicobacter or Clostridium. The bacterium can be present as a native, recombinant or inactivated bacterium or be comprised of various cleavage products. Bacterial cleavage products can constitute proteins, peptides, polysaccharides or nucleic acids from bacteria.

The parasite is preferably selected from the group consisting of Amaebida, Trypanosoma or Plasmodium.

The pharmaceutical composition according to the invention is preferably a vaccine composition and preferably comprises at least one virus, bacterium and/or a parasite and/or an antigen of a virus, bacterium and/or parasites. Therefore, all corresponding mixutes are also possible. The corresponding antigen from viruses, bacteria or parasites is selected from the same groups as described above for the pharmaceutical composition.

The pharmaceutical composition is preferably suitable for parenteral or mucosal administration and can additionally comprise an interleukin, interferon, another cytokine or mixture thereof.

Carriers and diluents customary for adjuvant preparations can for example be used as pharmaceutical carriers and diluents. The adjuvant content of the pharmaceutical compositions and the amounts of these compositions being administered will usually correspond to customary conditions.

As a result of its properties, the adjuvant according to the invention and/or the pharmaceutical composition produced from this is very well suited for prophylactic or therapeutic treatment of illnesses which are caused by various pathogens. Such illnesses can be for example: Early Summer Meningo-Encephalitis, Lyme disease, AIDS, Herpes infections, infections with Pseudomonas or Borrelia and others.

The adjuvant according to the invention can be administered to any subject, preferably a mammal, in which the immune response is to be stimulated, potentiated or the like.

With the adjuvant according to the invention and/or pharmaceutical composition produced therefrom, a suitable immune response in mammals, especially humans, can be stimulated by simultaneous sequential or parallel administration of the corresponding materials. Thereby, the immune response is especially directed against an infection caused by a pathogen. The adjuvant according to the invention and/or the pharmaceutical composition is preferably administered parenterally, but it is also suitable for mucosal administration, preferably for oral administration. The method for stimulating an immune response is preferably carried out in such a manner that a protective immune response is induced.

According to the invention the colloidal iron compound can be used for adjuvanting an antigen solution as well as for producing an adjuvant according to the present invention.

The adjuvant according to the invention is also useful for prophylactic or therapeutic treatment of diseases which are caused by various pathogens or it can be used for the production of a pharmaceutical composition which is useful for prophylactic or therapeutic treatment.

According to the present invention a method for the prophylactic or therapeutic treatment of diseases which are caused by a pathogen is also provided. This method is characterized in that the pharmaceutical composition according to the present invention is administered to a mammal. The protein and/or peptide and/or polysaccharide and/or nucleic acid is derived from said pathogen. The mammal can be a human or an animal and the administration of the pharmaceutical composition can be done as described earlier.

The invention is more precisely illustrated by the following examples, but is not limited to them.

EXAMPLE 1

Production of the iron compound in colloidal form 4.19 g of iron III citrate (Merck, Darmstadt, Germany) were dissolved in 100 ml bidist. water by stirring and heating. A 32% sodium hydroxide solution was added dropwise to this solution at room temperature and with rigorous stirring until a pH of 8.0 was obtained. Then, stirring was continued for 30 min. The colloid formed was centrifuged at high speed (30,000×g), the supernatant was discarded and the precipitate was resuspended in bidist. water (corresponding to the starting volume). Centrifugation and resuspension were repeated until the supernatant was colorless after centrifugation. The centrifuged material resuspended in water corresponding to the starting volume of iron citrate was pressed through a 0.45 μm sterile filter, and the sterile iron compound in colloidal form obtained in this manner was stored at 4° C. until use. Under these conditions the colloid was stable for more than 1 year.

EXAMPLE 2

Determination of the particle size of the colloid obtained according to Example 1

The particle size in nanometers was determined in a particle counting apparatus (ZetaSizer Type 4, Malvern, Worcestershire, England). In four independent experimental charges, particle sizes of around 200 nm were measured (Table 1). With the aid of atomic absorption measurements, the iron content of the colloids was determined (Table 1). On the average, the iron colloid preparations contained 7.6 millimol iron per liter. The viscosity of the iron colloid was determined by measuring the flow rate through a capillary. A 2 ml injection syringe equipped with a three-way stopcock and a cannula (23 G×1¼ inch) was filled with 2 ml of sample. After opening the stopcock, the time required for the outflow of the 2 ml sample was determined. It was shown that iron colloid had a lower flow-through rate in comparison to both water and a 0.2%0 aluminum hydroxide suspension such as is used for parenteral application. As is evident from Table 2, the flow-through rate of the iron colloid corresponds more to that of a 20% glycerol solution and a 10% protein solution respectively (bovine serum albumin, BSA) than to that of water. On the other hand, the flow through rate of a non colloidal gel suspension, e.g. aluminum hydroxide behaves similar to water.

TABLE 1

Properties of the iron colloid

| experiment number | particle size (nm) | Fe content (mmol/l) |
|---|---|---|
| #1 | 166 | 10.3 |
| #2 | 199 | 5.2 |
| #3 | 184 | 6.1 |
| #4 | 215 | 8.7 |
| average value | 191.0 | 7.6 |
| SD | 20.9 | 2.3 |

TABLE 2

Flow through time of 2 ml of sample through a cannula

| sample | flow through time absolute | flow through time with respect to water |
|---|---|---|
| water | 125 sec | — |
| 0.2% Al(OH)$_3$ | 136 sec | 11 sec |
| iron colloid | 246 sec | 121 sec |
| 10% BSA | 341 sec | 216 sec |
| 20% glycerol | 324 sec | 299 sec |

EXAMPLE 3

Protein adsorption

An iron colloid produced according to the invention as described in Example 1 was mixed with protein solutions of various concentrations. Purified human IgG was used as a model protein. The mixture was shaken at 4° C. for 16 hours or incubated while being rotated, and then centrifuged in a Heraeus Biofuge B for 30 min at 11,000 rpm and at a temperature of 4° C. The supernatant was subsequently examined for unbound protein by radial immunodiffusion according to the method of Mancini et al. (Immunochemistry 2 (1965) 235–254). The protein binding capacity of the iron colloid was determined by subtracting this value from the total amount of protein applied.

For purposes of comparison, an aluminum hydroxide solution adjusted to the same molar concentration as the iron colloid was also mixed with protein and treated in the same manner as described above.

Table 3 shows that the iron colloid according to the invention had a higher capacity to bind protein.

TABLE 3

Protein adsorption

| protein available | protein bound to iron colloid | | protein bound to aluminum hydroxide | |
|---|---|---|---|---|
| µg | µg | % bound | µg | % bound |
| 791 | 391 | 49 | 299 | 38 |
| 357 | 256 | 72 | 180 | 50 |
| 166 | 166 | 100 | 113 | 68 |

EXAMPLE 4

Intradermal application of iron colloid as adjuvant

The adjuvant properties of the iron colloid produced according to the invention were tested after intradermal application in balb/c mice. Five mice each per group were immunized with 20 ng of tetanus toxoid without adjuvants and with 20 ng of tetanus toxoid which was bound to iron colloid, respectively. For binding, 1 part tetanus toxoid solution was mixed with 9 parts iron colloid and incubated while being shaken for 16 h at 4° C. Two immunizations each were carried out with both preparations at intervals of 4 weeks. Two weeks after the second immunization, blood was taken from the mice and the serum was examined for tetanus toxoid antibody of the IgG class.

For this purpose, Nunc-MaxiSorp F96 ELISA plates were filled with 100 µl of a 10 µg/ml tetanus toxoid solution in carbonate buffer (pH 9.6). After 16 h of incubation at 4° C., unbound tetanus toxoid was aspirated and free binding sites on the plates were saturated with 2% BSA (bovine serum albumin) in PBS (phosphate buffered saltine). After incubation with the samples and with the internal positive control serum, respectively, at various dilutions (16 h/4° C.), incubation was carried out with peroxidase labeled goat-anti-mouse IgG (Accurate Chem., Westbury, N.Y., USA, 1:50,000 dilution) for 90 min at 37° C. and detection was carried out with ortho-phenylenediamine (3 mg/ml). The reaction was stopped with 2 N sulfuric acid before the measurement at 490 nm in a Nunc Immunoreader. The highest sample dilution with an optical density larger than 0.2 after the color reaction was used for the evaluation. The reciprocal value of this dilution corresponded to the titer of the sample.

Table 4 shows that the iron colloid strongly increased the immune response even at this small applied dose of tetanus toxoid.

TABLE 4

Intradermal application of iron colloid as adjuvant

| antigen | adjuvant | IgG anti-tetanus toxoid titer |
|---|---|---|
| 20 ng tetanus toxoid | — | 100 |
| 20 ng tetanus toxoid | iron colloid | 64000 |
| 0 ng (saline) | — | <50 |

EXAMPLE 5

Oral application of iron colloid as adjuvant

An increased immune response by the iron colloid produced according to the invention was examined after oral administration of TBE antigen of the Western subtype (FSME antigen, Immuno AG). For this purpose, C57/BL6 mice were immunized by intubation three times at one week intervals with FSME antigen alone and with antigen bound to iron colloid, respectively. (For preparation of the vaccine a mixture of equal volumes of FSME antigen solution in PBS and iron colloid were incubated for 16 h at 4° C.) Two weeks after the last immunization, blood and saliva was taken from the experimental animals and tested for antibodies of the IgG and IgA class against TBE with the aid of an enzyme immunoassay.

In order to test for antibody of the IgG class, Nunc-MaxiSorp F96 ELISA plates were filled with 100 µl of a 5 µg/ml FSME antigen solution in carbonate buffer,pH 9.6. After 16 h incubation at 4° C., unbound FSME antigen was aspirated and free binding sites on the plates were saturated with 2% BSA in PBS. After addition of the samples and the internal positive control serum, respectively, at various dilutions, incubation was carried out for 2 h at 37° C. Then peroxidase-labeled goat-anti-mouse IgG (Accurate Chem., Westbury, N.Y., USA, 1:150,000 dilution) was added, the samples were incubated for a further 90 min at 37° C. followed by addition of ortho-phenylenediamine (3 mg/ml).

The reaction was stopped with 2 N sulfuric acid before the measurement at 490 nm in the microtiter plate reader. The highest sample dilution whose optical density was larger than 0.2 after the color reaction was used for the evaluation. The reciprocal value of this dilution corresponded to the titer of the sample.

To test for antibodies of the IgA class, test sera or saliva were diluted 1:10 with PBS +1% BSA, mixed with a protein G Sepharose suspension (Pharmacia Biotech, Uppsala, Sweden) and incubated under shaking for 1 h in order to remove the majority of IgG antibodies form the sample by binding to protein G. Possible competition of IgG with the binding of IgA to the FSME antigen was thereby minimized during the following ELISA.

The enzyme immunoassay for IgA antibodies against TBE was carried out in analogy to the test for IgG. However, detection of the bound IgA was performed by reaction with a biotin labeled goat-anti-mouse IgA reagent (diluted 1:50, 000, 60 min/37° C., Southern Biotechnology, Birmingham, Ala., USA) and subsequently with peroxidase labeled streptavidin (Zymed, South San Francisco, Calif., USA, diluted 1:2,000, incubation: 60 min/37° C.).

Table 5 shows that the iron colloid increased the humoral immune response measured by antigen specific antibody titers. As expected, iron colloid administered alone did not lead to formation of specific antibodies.

TABLE 5

Oral application of iron colloid as adjuvant

| | | | FSME-specific antibody titer | |
|---|---|---|---|---|
| antigen | adjuvant | serum IgG | IgA | saliva IgA |
| 120 µg ESME antigen | — | 12800 | 640 | 80 |
| 120 µg FSME antigen | iron colloid | 25600 | 2560 | 160 |
| PBS | iron colloid | <100 | 20 | <20 |

COMPARATIVE EXPERIMENT 1

According to the method described in EP-363 835, an iron III chloride solution ($FeCl_3$, Merck, Darmstadt, Germany) was mixed with a sodium hydroxide solution by stirring until a pH of 7.0 was obtained. The material obtained in this manner is present as a precipitate (iron hydroxide gel)

To homogenize this precipitate—as also described in EP-363 835—an Ultra-Turrax® treatment was carried out. The particle size was determined to be 1.000 nm by a subsequent particle size measurement in the Malvern Zeta-Sizer. It was shown thereby that the iron hydroxide produced according to EP-363 835, even after an Ultra-Turrax® treatment, has no particle sizes of colloidal dimensions as given in the description of the present invention.

It could be shown by these comparative experiments that the iron hydroxide obtained according to EP-363 835 is present as a gel and not in the colloidal form according to the invention.

COMPARATIVE EXPERIMENT 2

The following experiment demonstrates the protein adsorption according to the invention in comparison to the protein absorption to an iron hydroxide according to EP-363 835 homogenized by Ultra-Turrax® treatment. The data obtained in the experiment are shown in the following Table A:

TABLE A

Protein adsorption (after adjustment to equal iron content)

| protein available | protein bound to iron colloid according to the invention | | protein bound to iron hydroxide gel according to EP-363 835 (after Ultra-Turrax ®) | |
|---|---|---|---|---|
| µg | in µg or | % bound | in µg or | % bound |
| 813 | 510 | 63 | 235 | 29 |
| 449 | 360 | 80 | 212 | 48 |
| 199 | 193 | 97 | 185 | 80 |

The above table clearly shows that at comparable iron contents of the two iron preparations and equal amounts of applied protein (especially in the upper range of protein content), more than double the amount of protein can be adsorbed by the colloid according to the invention than by the gel produced according to EP-363 835.

We claim:

1. An adjuvant consisting essentially of trivalent iron hydroxide compound in colloidal form with a particle size between 1 nm to 500 nm, wherein the adjuvant is sterile and is in the form of a water-in-oil emulsion.

2. A pharmaceutical composition comprising:
  (a) an adjuvant consisting essentially of trivalent iron hydroxide compound in colloidal form with a particle size between 1 nm to 500 nm;
  (b) at least one of an antigen, a protein, a peptide, a polysaccharide and an nucleic acid, wherein the preceding elements of (b) are derived from at least one of:
    (i) a virus selected from the group consisting of retroviruses, hepatitis viruses, flaviviruses, herpes viruses, influenza viruses, poxviruses, morbilliviruses, enteroviruses, polio viruses and paramyxoviruses;
    (ii) a bacterium selected from the group consisting of E. coli, Bordetella, Borrelia, Pseudomonas, Haemophilus, Mycobacterium, Streptococci, Salmonella, Helicobacter and Clostridium; or
    (iii) a parasite selected from the group consisting of Amebida, Trypanosoma and Plasmodium; and
  (c) at least one of an interleukin, an interferon or cytokine.

3. The pharmaceutical composition according to claim 2, characterized in that the virus is a whole virus, virus-like particle or virus cleavage product.

4. The pharmaceutical composition according to claim 2, wherein the virus is an inactivated virus, an attenuated virus or a recombinant virus.

5. A method for the treatment of a disease which is caused by a pathogen, comprising
  administering to a mammal an effective amount of a pharmaceutical composition comprising (a) an adjuvant consisting essentially of an iron hydroxide compound in colloidal form, wherein the iron hydroxide compound in colloidal form has a particle size between 1 nm and 500 nm, and (b) at least one of an antigen, a protein, a polypeptide, a polysaccharide and a nucleic acid, wherein the preceding elements of (b) are derived from the pathogen, wherein the administered composition can prevent or alleviate the symptoms of such disease.

6. A method for increasing the immunogenicity of an antigen, comprising the step of administering to a subject said antigen and an adjuvant solution consisting essentially of an iron hydroxide compound in colloidal form, wherein the iron hydroxide compound in colloidal form has a particle size between 1 nm to 500 nm.

7. The method according to claim 6, wherein the iron in the iron compound is present in a trivalent form.

8. The method according to claim 6, wherein said solution is aqueous.

9. The method according to claim 6, wherein said solution is a water-in-oil emulsion.

10. The method according to claim 6, wherein said iron compound in colloidal form has a particle size of about 200 nm.

11. A method for increasing the immunogenicity of an antigen, comprising the step of administering to a subject said antigen and an adjuvant solution comprising an iron hydroxide compound in colloidal form, wherein the iron hydroxide compound is obtained by altering the pH of a solution containing an iron salt of a weak acid to a range between 4.0 and 11.0.

12. The method according to claim 11, wherein said iron compound in colloidal form has a particle size ranging from 1 nm to 500 nm.

13. The method according to claim 12, wherein said iron compound in colloidal form has a particle size ranging from 100 nm to 500 nm.

14. The method for increasing the immunogenicity of an antigen according to claim 11, wherein the pH value is altered to a pH between 6.8 to 9.0.

15. The method for increasing the immunogenicity of an antigen according to claim 14, wherein the pH value is altered to a pH between 7.0 to 8.5.

* * * * *

UNITED STATES PATENT AND TRADEMARK OFFICE
CERTIFICATE OF CORRECTION

PATENT NO. : 5,895,653
DATED : April 20, 1999
INVENTOR(S) : Johann EIBL et al.

It is certified that error appears in the above-identified patent and that said Letters Patent is hereby corrected as shown below:

On the title page,

Please delete the following information on the face of the patent: [73] Assignee: Tempo G. Los Angeles, Calif., and insert:

--[73] Assignee: Bio-Products & Bio-Enginnering Aktiengesellschaft--.

Please delete the following information on the face of the patent: Attorney, Agent, or Firm - Thomas I. Rozsa; Toney D. Chen; Jerry Fong, and insert:

--Attorney, Agent, or Firm - Foley & Lardner--.

Signed and Sealed this

Twenty-eighth Day of September, 1999

Attest:

Q. TODD DICKINSON

*Attesting Officer*   *Acting Commissioner of Patents and Trademarks*